United States Patent

Ruf

Patent Number: 5,286,284
Date of Patent: Feb. 15, 1994

[54] HYDRAZINIUM SULPHOSALICYLATE, ITS PREPARATION AND ITS USE AS AN ANTIOXIDIZING STABILIZER FOR TIN(II) COMPOUNDS

[76] Inventor: Erich Ruf, Auf'm Gartenstück 10, 4300 Essen-Haarzopf, Fed. Rep. of Germany

[21] Appl. No.: 991,654

[22] Filed: Dec. 16, 1992

Related U.S. Application Data

[62] Division of Ser. No. 615,223, Nov. 19, 1990, Pat. No. 5,202,470.

[30] Foreign Application Priority Data

Nov. 20, 1989 [DE] Fed. Rep. of Germany ....... 3938472.1

[51] Int. Cl.$^5$ .................. C25D 3/32; C07C 317/46
[52] U.S. Cl. .................. 106/1.25; 205/173; 423/265
[58] Field of Search ............ 423/265, 266; 205/173; 106/1.25

[56] References Cited

U.S. PATENT DOCUMENTS 2,852,557 9/1958 Schraufstatter ............ 260/519
5,202,470 4/1993 Ruf ............ 562/429

FOREIGN PATENT DOCUMENTS 3533788 11/1986 Fed. Rep. of Germany.

*Primary Examiner*—Michael Lewis
*Assistant Examiner*—Stephen G. Kalinchak
*Attorney, Agent, or Firm*—Anderson Kill Olick & Oshinsky

[57] ABSTRACT

The invention provides a compound of the formula $$[NH_2NH_2]_a[C_6H_3(COOH)(SO_3H)(OH)]_b$$

wherein
a is 1 and
b is from 1 to 2.

The compound is useful for stabilizing tin (II) compounds against oxidation, in particular in the electrolytic coloring of aluminum or aluminum alloys.

3 Claims, No Drawings

HYDRAZINIUM SULPHOSALICYLATE, ITS PREPARATION AND ITS USE AS AN ANTIOXIDIZING STABILIZER FOR TIN(II) COMPOUNDS

This is a divisional application of Ser. No. 07/615,223, filed Nov. 19, 1990, now U.S. Pat. No. 5,202,470.

The invention relates to hydrazinium sulphosalicylate, a process for its preparation and its used as an antioxidising stabilizer for tin(II) compounds and solutions thereof.

Tin can be either divalent or tetravalent in its compounds. Although divalent tin compounds are easy to prepare, they oxidise readily, especially in an aqueous phase, to give tetravalent tin compounds. For this reason, divalent tin compounds, such as, for example, tin-(II) chloride, are therefore also used as reducing agents. It is of particular advantage here that divalent tin is a good reducing agent both in acid and in alkaline solution.

If divalent tin compounds are used in industrial processes, it is therefore necessary to suppress the oxidation of divalent tin to tetravalent tin as far as possible by addition of a suitable stabilizer. Thus, for example, in the case of electrolytic two-stage processes for colouring aluminium or aluminium alloys with sulphuric acid electrolytes containing tin(II) sulphate, it is necessary to add antioxidising stabilizers so that the divalent tin is retained for as long as possible, since only this species can be used for electrolytic colouring.

A large number of stabilizers for divalent tin compounds in industrial applications is known from the literature. Organic sulphonic acids, such as, for example, phenol- or cresolsulphonic acid, are often employed for this purpose, thus, for example, in the electrolytic colouring of aluminium or aluminium alloys with electrolytes containing tin(II) sulphate, especially when sulphuric acid tin(II) sulphate solutions are used.

However, these organic sulphonic acids just mentioned have disadvantages. Both acids are toxic and cause a severe odour nuisance, last but not least because there may be a free phenol or cresol content. If such compounds enter the effluent, they cause severe pollution of the effluent, since on the one hand they are difficult to degrade biologically and on the other hand they have a high chemical and biological oxygen demand or a high permanganate value.

The stabilizing action, namely of phenolsulphonic acid, is moreover only low. In addition, no deepening in colour can be achieved with either of the two sulphonic acids in the electrolytic colouring of aluminium or aluminium alloys.

The invention is therefore based on the object of discovering compounds which are ecologically and physiologically acceptable, readily accessible stabilizers of improved activity for divalent tin compounds. They should prevent oxidation of tin(II) compounds and achieve an improvement in the colour intensity in electrolytic colouring of aluminium or aluminium alloys.

Surprisingly, this object can be achieved by hydrazinium sulphosalicylate of the formula

$$[NH_2NH_2]_a[C_6H_3(COOH)(SO_3H)(OH)]_b$$

wherein
a is 1 and
b is from 1 to 2.

It has been found that hydrazinium sulphosalicylate compounds can be precipitated as sparingly soluble compounds from an aqueous phase at room temperature. This precipitation of hydrazinium sulphosalicylates is surprising to the expert in as much as other sulphonic acids, such as, for example, toluenesulphonic acid, phenolsulphonic acid, cresolsulphonic acid, methanesulphonic acid, hydroxyethanesulphonic acid, amidosulphonic acid and sulphosuccinic acid, do not result in such precipitates under the same operating conditions.

The ratio of hydrazine to sulphosalicylic acid in the hydrazinium sulphosalicylates according to the invention varies in a range from 1:1 to 1:2. The hydrazinium disulphosalicylate formed in a reaction of $\geq 1:2$ is preferred.

The compounds can be isolated from the reaction mixture simply by filtration. Varying amounts of water are bound in the product, as a rule 0 to 2 mol of water, depending on the drying conditions.

The products according to the invention are pulverulent, easy to handle and odourless.

The invention also relates to a process for the preparation of the abovementioned compounds. The process according to the invention is characterized in that sulphosalicylic acid and/or its hydrate is reacted with hydrazine and/or its hydrate in a ratio of 1:1 to 3:1 in an aqueous medium at temperatures of 5 to 60° C.

The process for the preparation of hydrazinium sulphosalicylates can be carried out in a very simple manner, for example by initially introducing an aqueous sulphosalicylic acid into the reaction vessel and adding a hydrazine hydrate solution, while stirring.

For quantitative precipitation, it is necessary to carry out the reaction at relatively low temperatures. The lower the operating temperature, the more sparingly soluble such hydrazinium sulphosalicylate compounds become. Precipitation virtually no longer occurs above 60° C. To effect as complete as possible a precipitation of hydrazinium sulphosalicylate, it is appropriate to use relatively concentrated sulphosalicylic acid solutions and to carry out the reaction at 20° C., or preferably at even lower temperatures.

Virtually no precipitation is obtained if a molar ratio of sulphosalicylic acid to hydrazine of less than 1:1 is used. It is therefore advantageous to add a small excess of sulphosalicylic acid over hydrazine in a precipitation reaction in order thus to effect complete precipitation of the hydrazine.

The use of at least 2 mol of sulphosalicylic acid per mole of hydrazine hydrate is preferred in such a precipitation reaction, so that hydrazinium disulphosalicylate is obtained as the preferred precipitation product. If larger amounts of sulphosalicylic acid are used, small amounts of sulphosalicylic acid are bound in the precipitate by absorption. In principle, the excess sulphosalicylic acid can be removed from the precipitation product by washing. However, this is not necessary for the use as an antioxidising stabilizer for tin(II) compounds.

The filtrate which is obtained after removal of the precipitate and which contains excess sulphosalicylic acid can in turn be used for dissolving fresh sulphosalicylic acid for a further precipitation reaction.

This operation can be performed several times if the sulphosalicylic acid employed is pure, so that a simple and very economical process is provided for the preparation of hydrazinium sulphosalicylate compounds.

The hydrazinium sulphosalicylates contain water, depending on the nature of the drying. Hydrazinium disulphosalicylate, the precipitation product from a 1:2 reaction of hydrazine and sulphosalicylic acid, still contains, for example, 1 mol of water after drying in vacuo at a maximum of 60° C. for several hours.

In principle, hydrazinium sulphosalicylates can also be obtained by evaporation of a solution containing the individual components in appropriate proportions. However, the product from the precipitation process is superior in its action to the product obtained as an evaporation residue.

The invention moreover relates to the use of the hydrazinium sulphosalicylate as hereinbefore for stabilizing tin(II) compounds. Accordingly the invention provides a process for stabilising a tin (II) compound which comprises adding to the compound, or to a solution or composition containing it, a hydrazinium sulphosalicylate as hereinbefore defined.

Surprisingly, the hydrazinium sulphosalicylate precipitation products exhibit an improved antioxidising action, in comparison with the sulphonic acids customary as a stabilizer, when added to tin(II) compounds, in solid or 5 in dissolved form..They largely suppress the oxidation of tin(II) compounds to tetravalent tin.

If hydrazinium sulphosalicylates are admixed to solid tin(II) sulphate, usually in the order of 30 to 40% by weight, this mixture remains unchanged even during prolonged storage in closed drums.

If this mixture is dissolved in dilute sulphuric acid analogously to the preparation of a sulphuric acid tin(II) sulphate solution in the electrolytic colouring of aluminium or aluminium alloys, surprisingly no sparingly soluble hydrazinium sulphate precipitates during this operation. Rather, a clear solution which, because of the hydrazinium sulphosalicylate content, has a very good antioxidation-stabilizing action is obtained. At the same time, in sulphuric acid electrolytes containing tin(II) sulphate, hydrazinium sulphosalicylate furthermore also improves the colour intensity in the electrolytic colouring of aluminium or aluminium alloys in comparison with a sulphuric acid tin(II) sulphate solution with no added hydrazinium sulphosalicylate. In a further aspect, therefore, the invention provides a solution suitable for the electrolytic colouring of aluminium or an alloy thereof, the solution comprising a tin (II) comopund and, as stabiliser therefor, a hydrozinium sulphosalicylate as hereinbefore defined.

Hydrazinium sulphosalicylate stabilizers can also be added as highly active antioxidation stabilizers to other divalent tin compounds or solutions thereof, such as, for example, tin(II) fluoroborate solution or tin(II) methanesulphonate solution.

Hydrazinium sulphosalicylates have relatively low solubilities in hydrochloric acid solutions and solutions containing metal chloride, the solubility being reduced as the hydrochloric acid or metal chloride content increases. The same also applies to solutions containing methanesulphonic acid or corresponding metal salts. In contrast, hydrazinium sulphosalicylates are readily soluble in dilute sulphuric acid solutions.

Dilute sulphuric acid solutions such as are also customarily used for industrial application in electrolytic colouring processes for aluminium or aluminium alloys are therefore preferably used as aqueous media.

The invention will be further described in the Examples which follow.

EXAMPLE 1 a) Precipitation process for the preparation of hydrazinium sulphosalicylate 100 ml of water are initially introduced into a 1 l four-necked flask provided with a stirrer, thermometer, reflux condenser and dropping funnel, and 258 g of sulphosalicylic acid dihydrate are dissolved in this. The solution is thermostatically controlled at 16° C. 104.3 g of a 24% strength hydrazine hydrate solution are then added to this solution in portions. The solution is stirred for 30 minutes, while cooling to 16° C. The thick but still flowing crystal sludge is then filtered off over a suction filter (black band filter). The filter cake thus obtained is dried at 60° C. in vacuo (30 mmHg) for about 6 hours. Yield: 232 g.

In the context of the filtration, 90 ml of filtrate are obtained and are returned to the abovementioned 1 l four-necked flask. 100 ml of water are added to this filtrate. 258 g of sulphosalicylic acid dihydrate are dissolved in this volume of liquid, while stirring. After addition of 104 g of a 24% strength hydrazine hydrate solution in portions, while cooling to 16° C., and stirring for 30 minutes, the precipitation product is separated off, as described above, and the filter cake is dried at 60° C. in vacuo (30 mmHg) for about 6 hours. Yield: 225 g.

180 ml of filtrate are obtained in this procedure, are returned again to the 1 l four-necked flask to which 10 ml of water are then added. 258 g of sulphosalicylic acid dihydrate are dissolved in this volume of liquid, while stirring, 104.3 g of a 24% strength hydrazine hydrate solution are added in portions at 16° C., while stirring, the precipitation product is separated off, as described above, and the filter cake is dried at 60° C. in vacuo (30 mmHg) for about 6 hours. Yield: 241 g. 200 ml of filtrate are obtained. 258 g of sulphosalicylic acid dihydrate are dissolved in this filtrate, while stirring, and, by the procedure described above, 104 g of a 24% strength hydrazine hydrate solution are added, the product is separated off and the filter cake is dried at 60° C. in vacuo (30 mmHg) for about 6 hours. Yield: 227 g.

This process can be continued as long as no substantial enrichment of impurities takes place in the filtrate. The product dried in the manner described has the following composition:

| | |
|---|---|
| Water | 4.0% by weight |
| Sulphosalicylic acid | 89.5% by weight |
| Hydrazine | 6.5% by weight. |

This product can be mixed in the solid form with crystalline tin(II) sulphate in any desired ratio and the mixture can be stored in a closed vessel for a relatively long time without a change taking place in the mixture.

b) Evaporation process for the preparation of hydrazinium sulphosalicylate 200 ml of water are initially introduced into a 1 l four-necked flask provided with a stirrer, thermometer, reflux condenser and dropping funnel, and 258 g of sulphosalicylic acid dihydrate are dissolved in this. 104.3 g of a 24% strength hydrazinium hydrate solution are added to this solution in portions, while stirring and cooling to 16° C. All of the water is then evaporated off in vacuo, while stirring. Yield: 242 g.

c) Antioxidising stabilization of tin(II) compounds 1 l of a sulphuric acid tin(II) sulphate solution containing 16 g of $H_2SO_4$ per l and 14 g of $SnSO_4$ per l is prepared in a 1 l powder bottle of glass (solution a).

800 ml of an aqueous sulphuric acid solution containing 16 g of $H_2SO_4$ 1 l are initially introduced into a further 1 l powder bottle of glass 20 g of a previously prepared mixture of 14 g of tin(II) sulphate and 6 g of hydrazinium disulphosalicylate are dissolved in this, while stirring. Thereafter, the solution is made up to 1 l with water (solution b).

After covering with a watch glass, the two solutions are left to stand at room temperature for 7 days at the same time. After 7 days, the resulting precipitate of tin(IV) compounds is filtered off from the two solutions and dried and its weight is determined. 513 mg of precipitate are determined from solution a (no stabilizer) and 30 mg from solution b (containing stabilizer). Hydrazinium disulphosalicylate thus largely suppresses the oxidation of divalent tin to tetravalent tin.

d) Electrolytic colourings

Electrolytic colourings of in each case an AlMg1 sheet (50×100×1 mm) are performed with both solutions. The sheets coloured in this way are analysed with a colorimeter (Minolta Chromameter). The following values are obtained here:

|  | L | a | b |
|---|---|---|---|
| Solution a | 37.3 | 2.4 | −14.8 |
| Solution b | 26.0 | 2.4 | 4.8 |

As can be seen from the L values (high L values denote lighter colour shades, lower L values denote darker colour shades), solution b containing hydrazinium sulphosalicylate gives a more intense colour than solution a containing no hydrazinium sulphosalicylate.

EXAMPLE 2

1 l of tin(II) methanesulphonate solution containing 7.44 g of divalent tin per l is initially introduced into each of two 1.5 l powder bottles of glass. 6 g of hydrazinium disulphosalicylate containing 1 mol of water of crystallization are also added to one of the solutions (solution b). Since the hydrazinium disulphosalicylate stabilizer is not completely soluble in solution b, the solution is filtered. Air is passed through the two solutions at room temperature under the same conditions. After 264 hours of uninterrupted passage of air, no divalent tin is found in solution a (no stabilizer), but 6.80 g of divalent tin per l are still found in solution b (containing stabilizer).

EXAMPLE 3

1 l of tin(II) fluoborate solution containing 7.64 g of divalent tin per l is introduced into each of two 1.5 l powder bottles of glass. 6 g of hydrazinium disulphosalicylate containing 1 mol of water of crystallization are also added to one of the solutions (b).

Air is passed through the two solutions in the same manner. After 264 hours of uninterrupted passage of air, 5.32 g of divalent tin per l are still found in solution a (containing no stabilizer) but 6.80 g of divalent tin per l are still found in solution b (containing stabilizer).

I claim:

1. A process for stabilising a tin (II) compound which comprises adding to the compound, or to a solution or composition containing it, a hydrazinium sulphosalicylate of the formula $$[NH_2NH_2]_a[2C_6H_3(COOH)(SO_3H)(OH)]_b$$

wherein a is 1 and b is from 1 to 2.

2. A process according to claim 1 wherein the tin (II) compound is tin (II) sulphate, tin (II) fluoroborate or tin (II) methanesulphonate.

3. A solution suitable for the electrolytic colouring of aluminum or an alloy thereof, the solution comprising a tin (II) compound and, as stabilizer therefor, a hydrazinium sulphosalicylate of the formula $$[NH_2NH_2]_a[C_6H_3(COOH)(SO_3H)(OH)]_b$$

wherein a is 1 and b is from 1 to 2.

* * * * *